US00PP34734P2

(12) United States Plant Patent
de Groot

(10) Patent No.: US PP34,734 P2
(45) Date of Patent: Nov. 15, 2022

(54) GROUNDCOVER ROSE PLANT NAMED 'RUIRJ0078A'

(50) Latin Name: *Rosa hybrida*
Varietal Denomination: RUIRJ0078A

(71) Applicant: De Ruiter Intellectual Property B.V., Amstelveen (NL)

(72) Inventor: Hendrikus Cornelis Adrianus de Groot, Amstelveen (NL)

(73) Assignee: De Ruiter Intellectual Property B.V.

( * ) Notice: Subject to any disclaimer, the term of this patent is extended or adjusted under 35 U.S.C. 154(b) by 0 days.

(21) Appl. No.: 17/841,374

(22) Filed: Jun. 15, 2022

(51) Int. Cl.
*A01H 5/02* (2018.01)
*A01H 6/74* (2018.01)

(52) U.S. Cl.
USPC ..... Plt./101

(58) Field of Classification Search
USPC ..... Plt./101, 102
See application file for complete search history.

*Primary Examiner* — Susan McCormick Ewoldt
(74) *Attorney, Agent, or Firm* — Cassandra Bright

(57) ABSTRACT

A new and distinct groundcover *Rosa* plant named 'RUIRJ0078A' is disclosed, characterized by double, medium pink flowers on rapidly growing, thornless plants. Plants are compact and low growing, suitable for groundcover use. Hips have not been observed to be produced. The new variety is a *Rosa*, normally produced as an outdoor garden or container plant.

1 Drawing Sheet

Latin name of the genus and species: *Rosa hybrida.*
Variety denomination: 'RUIRJ0078A'.

BACKGROUND OF THE INVENTION

The new *Rosa* cultivar is a product of a planned breeding program conducted by the inventor. The cross resulting in this new variety was made in April of 2009 at a nursery in Boskoop, The Netherlands.

The seed parent is the unpatented variety *Rosa* 'Louise Bugnet'. The pollen parent is the unpatented variety *Rosa* 'BOKRATRACK'. The new variety was selected in July of 2012 by the inventor at the same nursery in Boskoop, The Netherlands. The inventor continued observing characteristics of the new variety for several years, in the controlled conditions of the research nursery.

Asexual reproduction of the new cultivar was performed by vegetative softwood cuttings. This was first performed at a greenhouse in Amstelveen, The Netherlands, in September 2012, and has shown that the unique features of this cultivar are stable and reproduced true to type in successive generations.

SUMMARY OF THE INVENTION

The cultivar 'RUIRJ0078A' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'RUIRJ0078A' These characteristics in combination distinguish 'RUIRJ0078A' as a new and distinct *Rosa* cultivar:

1. Groundcover shrub rose.
2. Abundant medium pink double flowers.
3. No hips produced.
4. Rapid growth.
5. Thornless.

PARENTAL COMPARISON

Plants of the new cultivar 'RUIRJ0078A' are similar to plants of the seed parent in most horticultural characteristics, however, plants of the new cultivar 'RUIRJ0078A' differ in the following:

1. Flowers of the new cultivar have a darker pink coloration than flowers of the seed parent.
2. Plants of the new cultivar do not produce hips, as do plants of the seed parent.

Plants of the new cultivar 'RUIRJ0078A' are similar to plants of the pollen parent in most horticultural characteristics, however, plants of the new cultivar 'RUIRJ0078A' differs in the following;

1. Flowers of the new cultivar are lighter pink than flowers of the pollen parent.
2. The new cultivar produces more petals per flower than plants of the pollen parent.
3. Plants of the new cultivar are more compact and dense than plants of the pollen parent.

COMMERCIAL COMPARISON

Plants of the new cultivar 'RUIRJ0078A' can be compared to the commercial variety *Rosa* 'Pink Grootendorst', unpatented. These cultivars are similar in most horticultural characteristics, however 'RUIRJ0078A' differs in the following:

1. This new cultivar produces larger flowers than this comparator.
2. This new cultivar does not have thorns; this comparator produces thorns.
3. The new cultivar is more compact than this comparator.

Plants of the new cultivar 'RUIRJ0078A' can be compared to the commercial variety *Rosa* 'Risausma', unpatented. These cultivars are similar in most horticultural characteristics, however 'RUIRJ0078A' differs in the following:

1. This new cultivar has darker pink flowers than this comparator.
2. This new cultivar does not have thorns; this comparator produces thorns.
3. The new cultivar is more compact than this comparator.
4. Flowers of the new cultivar do not fade with age as do flowers of this comparator.

BRIEF DESCRIPTION OF THE PHOTOGRAPH

The accompanying photograph illustrates a close up view of a flower. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'RUIRJ0078A' plants grown outdoors in Camarillo, Calif. The growing temperature ranged from approximately 15° C. to 28° C. during the day and from approximately 8° C. to 15° C. during the night. Measurements were taken in April and May. General light conditions were very bright, normal sunlight. Measurements and numerical values represent averages of typical plant types.

Botanical classification: *Rosa* 'RUIRJ0078A'.

Market classification: Groundcover shrub rose.

PROPAGATION

Time to initiate roots: 10 days at approximately 25° C.

Time to produce a rooted cutting: 21 days at approximately 25° C.

PLANT

Growth habit: Dense, low growing, groundcover type.

Age of plant described: 1 year.

In a container size: 2 gallon.

Height: 50 cm.

Plant spread: 55 cm.

Branching characteristics:

Length of primary lateral branches: Approximately 14 cm to 25 cm.

Diameter of lateral branches: Approximately 9 mm.

Quantity of lateral branches: 15 to 22 within 6 weeks of emerging from dormancy.

Branching arrangement: Dense, compound.

Branches—young wood:

*Diameter*.—Approximately 4 mm.

*Texture*.—Smooth to very slightly pubescent.

*Approximately density/quantity of thorns*.—No thorns on newest growth. Approximately 5 to 7 very soft thorns per 1 linear cm on some intermediate growth.

*Color*.—Near RHS Yellow-Green N145A.

Branches—old wood:

*Diameter*.—Approximately 5 mm to 6 mm.

*Color*.—Near RHS Greyed-Purple 187B.

*Texture*.—Smooth.

*Internode*.—2.5 cm to 3.5 cm.

Thorns: Not observed.

FOLIAGE

Leaf:

*Arrangement*.—Imparipinnate.

*Quantity*.—Approximately 9 to 12 per main branch.

*Average length*.—Approximately 10 cm to 13 cm.

*Average width*.—Approximately 6.5 cm.

Leaflet:

*Quantity*.—Most commonly 7 per leaf. Rarely 3 or 5.

*Average length*.—Approximately 3.5 cm to 4.5 cm.

*Average width*.—Approximately 2.0 cm.

*Shape of blade*.—Elliptic.

*Apex*.—Acute.

*Base*.—Broad tapered.

*Margin*.—Very finely serrate.

*Texture of top surface*.—Smooth.

*Texture of bottom surface*.—Smooth.

*Pubescence*.—None observed.

*Leaf internode length*.—2.5 cm to 3 cm.

*Color*.—Young foliage upper side: Near RHS Yellow-Green 144A. Young foliage under side: Near RHS Yellow-Green 144A. Mature foliage upper side: Near RHS Green 137B. Mature foliage under side: Near RHS Green 137C.

*Venation*.—Type: Pinnate. Venation color upper side: Near Yellow-Green 144C. Venation color under side: Near Yellow-Green 145A.

Stipule:

*Length*.—1.7 cm.

*Width*.—4 mm.

*Color*.—Near RHS Green 137D.

*Texture*.—Smooth.

Petiole:

*Length*.—3.0 cm.

*Width*.—3 mm.

*Color*.—Near RHS Yellow-Green 144C.

*Texture*.—Glabrous.

Rachis:

*Length*.—5.5 cm.

*Width*.—2 mm.

*Color*.—Near RHS Yellow-Green 144A.

*Texture*.—Glabrous.

FLOWER

Natural flowering season: April through October in Southern California.

Begins flowering after how many years/months: 2 months.

Inflorescence type: Multiflora.

Rate of flower opening: Approximately 3 days from bud to fully opened flower.

Flower longevity on plant: 3 to 4 days, after fully opened.

Quantity of flowers: 1 to 4 flowers per flowering axil.

Inflorescence size:

*Diameter*.—Approximately 10 cm.

*Height*.—Approximately 6 cm.

Flower size:

*Diameter*.—Approximately 7.0.

*Height*.—Approximately 4.0 cm.

Peduncle:
*Length.*—2.0 cm to 3.5 cm.
*Diameter.*—3 mm.
*Color.*—Near RHS Yellow-Green 144B.
*Texture.*—Glabrous.

Petals:
*Petal arrangement.*—Loose radial.
*Length.*—3.5 cm.
*Width.*—3.2 cm.
*Shape.*—Obcordate.
*Margin.*—Entire, slightly undulate.
*Apex.*—Retuse.
*Base.*—Cuneate.
*Petal quantity.*—25 to 35.
*Texture.*—Glabrous all surfaces.
*Color.*—When opening: Upper surface: Near RHS Red-Purple 70B, lightly streaked 69B towards base. Base White N155B. Lower surface: Near RHS Red-Purple 70B, lightly streaked 69B towards base. Base White N155B. Fully opened: Upper surface: Near RHS Red-Purple 72D, lightly streaked 69B towards base. Base White N155B. Lower surface: Near RHS Red-Purple 72D, lightly streaked 69B towards base. Base White N155B. Color Changes when aging: None.

Bud:
*Shape.*—Ovate.
*Length.*—Approximately 2.5 cm.
*Diameter.*—Approximately 1.5 cm.
*Color.*—Near RHS Red-Purple 67A.

Sepals:
*Quantity.*—5.
*Length.*—2.5 cm.
*Width.*—8 mm at base.
*Shape.*—Very narrow deltoid.
*Color.*—Interior Surface: Near Green 138B. Exterior Surface: Near Green 138B.
*Texture.*—Smooth.

Receptacle:
*Length.*—8 mm.
*Width.*—8 mm.
*Shape.*—Spherical.
*Color.*—Near Green 138A.

Fragrance: Moderately strong, sweet rose scent. Very slightly spicy.

REPRODUCTIVE ORGANS

Stamens:
*Quantity.*—Average 150.
*Filament length.*—Average range 7 mm to 11 mm.
*Filament color.*—White 155C.

Anthers:
*Length.*—2 mm.
*Shape.*—Oblong.
*Color.*—RHS Greyed-Orange 167C.
*Pollen.*—Scant, colored near Greyed-Orange 167C.

Pistil:
*Number.*—30 to 40.
*Length.*—3 mm.
*Style.*—Length: Approximately 3 mm. Color: Near RHS Yellow 4D.

Stigma:
*Shape.*—Orbicular.
*Color.*—RHS Yellow 4C.

OTHER CHARACTERISTICS

Seeds and fruits: Not observed.

What is claimed is:

1. A new and distinct Groundcover Rose plant named 'RUIRJ0078A' as herein illustrated and described.

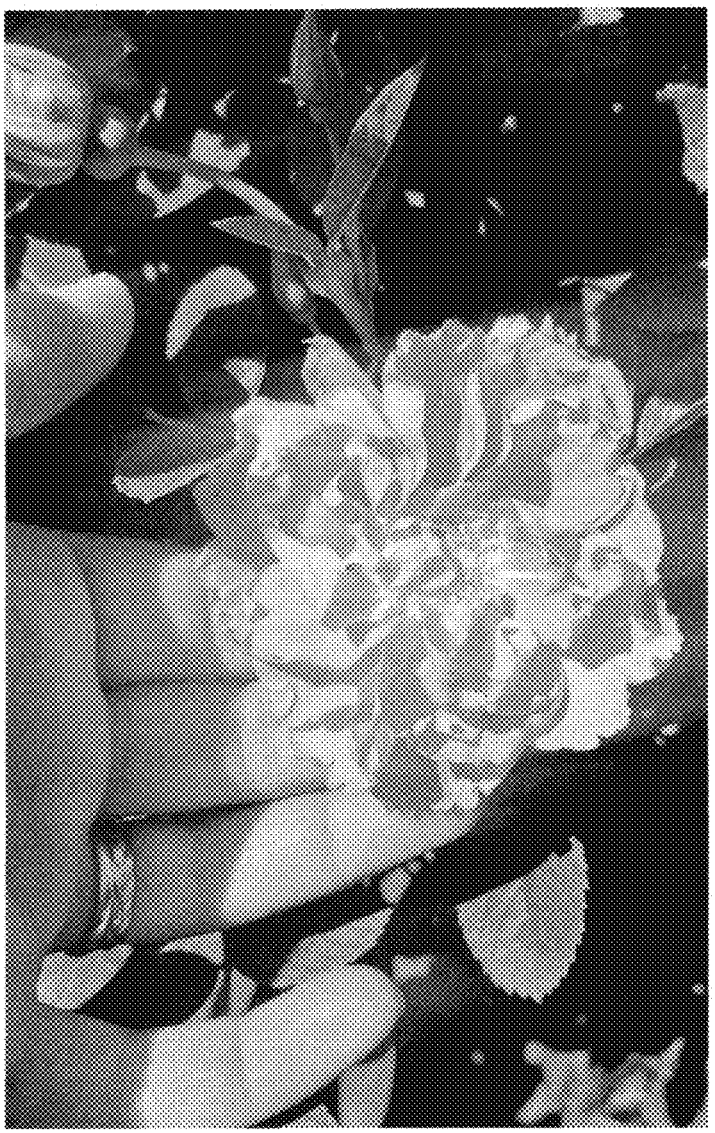

* * * * *